United States Patent [19]
Hansen

[11] 3,992,265
[45] Nov. 16, 1976

[54] ANTIBIOTIC SUSCEPTIBILITY TESTING

[75] Inventor: Lloyd Frank Hansen, Campbell Hall, N.Y.

[73] Assignee: American Cyanamid Company, Stamford, Conn.

[22] Filed: Dec. 31, 1975

[21] Appl. No.: 645,581

[52] U.S. Cl. .......................... 195/127; 195/103.5 R
[51] Int. Cl.² .......................................... C12K 1/10
[58] Field of Search ............ 195/127, 103.5 R, 139; 23/259, 292

[56] References Cited
UNITED STATES PATENTS

| | | | |
|---|---|---|---|
| 3,441,383 | 4/1969 | Moore et al. ......................... | 23/259 |
| 3,776,817 | 12/1973 | Van Der Pfordten .............. | 195/127 |

*Primary Examiner*—Alvin E. Tanenholtz
*Attorney, Agent, or Firm*—Samuel Branch Walker

[57] ABSTRACT

The susceptibility of microorganisms to various antibiotics is determined by propagating microorganisms in the presence of different concentrations of the antibiotic in a plurality of test cells or chambers axially aligned on one element of a cylinder of plastic which cylinder has a concentric protective sleeve with apertures to match the test cups and indexing and orienting means to keep the sleeve and cylinder aligned. A series of concentrations of a particular antibiotic are prepackaged and stored dry in the test cells of a particular cylinder with various antibiotics in various cylinders which may be positioned in a storage rack for convenience in inoculation and incubation.

6 Claims, 10 Drawing Figures

ANTIBIOTIC SUSCEPTIBILITY TESTING

BACKGROUND OF THE INVENTION

This invention relates to antibiotic susceptibility testing and more particularly a test assembly of a series of hollow cups in which cups are placed various concentrations of various antibiotics or other therapeutic control agents to ascertain the interaction between such control agents and various microorganisms, usually pathogenic. With the proliferation of antiobiotics and other drugs both in the hospital and in the laboratory as well as educational institutions there is an increasing demand for information concerning the susceptibility or sensitivity of a particular microorganism to various antibiotics or drugs.

PRIOR ART

The use of automated analytical prodedures has become of increasing importance. For both chemical and biological procedures the number of samples to be run has been increasing exponentially as new procedures are developed, and existing procedures are adapted to large quantity requirements.

U.S. Pat. No. 3,301,065 — LIQUID SAMPLE SUPPLY APPARATUS, Fahrenbach, Bell and Sandage, Jan. 31, 1967, shows an automatic sampling system in which a series of cups containing samples are fed serially into an analytical system. The samples may be in cups on a spiral in a plate, or may be fed as a series of individual pallets locked together and fed along a belt. Locking the pallets together insures coordination in feeding separate pallets.

Belgium Pat. No. 691,532, Feb. 28, 1967, shows lyophilized antibiotics or chemotherapeutic agents in various concentrations, including a blank, in separate cells arranged in columns and rows in a tray, for testing the resistance of microorganisms to antibiotics or agents. Retaining appendices project from the base of the culture cells to retain the lyophilized material in the individual cells. Identifying covers cooperate with each cell to close, and identify the contents of, each cell. A culture medium and/or indicator may be present in the lyophilized state in the test cells. The cells and the covers are essentially transparent to permit observation of the cultures.

U.S. Pat. No. 3,713,985 — DEVICE AND METHOD FOR TESTING POTENCY OF BIOLOGICAL CONTROL REAGENTS, Astle, Jan. 30, 1973 shows a series of biological reagents in a series of cups, in a strip, or pallet, with the strips having dovetails to longitudinally lock a group of the strips together to form a tray. A foil cover to protect lyophilized contents during storage is disclosed, with reconstitution of the contents at time of use.

U.S. Pat. No. 3,890,201 — MULTI-CHAMBER IMPEDANCE MEASURING MODULE-CAP COMBINATION, Cady, June 17, 1975, shows rows and columns of upstanding cylinders on a flat base, forming cells, with electrically conductive strips in each cell to permit impedance measurement of the cell contents. The impedance in the cell is a function of microorganism growth. Separate caps are provided for each cell to permit gas flow into the individual cells during incubation.

SUMMARY OF THE INVENTION

It has now been found that the susceptablity of various microorganisms to antibiotics can be particularly conveniently determined by using an antibiotic susceptability testing cylinder which is a transparent solid cylinder of a biologically inert plastic such as a polymer of methyl methacrylate, or a vinyl resin, which may be of any biologically inert transparent or nearly transparent plastic, which cylinder has along one cylindrical element parallel to its axis, a series of hollow cups. The cups may be either molded into the plastic or drilled into the plastic. On small runs, a transparent rod may be conveniently turned to size and the cups drilled therein. On larger runs, it is convenient to use a molding process in which the cylinder has a slight draft or taper, of about 1° to 3° to permit the cylinder to be withdrawn from its mold, and in which the hollow cups may be molded using suitable pins. The hollow cups may be drilled into the plastic. The more complex molding techniques increase the cost of the mold, but reduce production costs—hence depending upon the size of the contemplated run those skilled in the art can choose a manufacturing technique which minimizes overall costs.

On this cylinder is a transparent sleeve of similar plastic which is rotatable so that by having a series of loading apertures along one element of the sleeve, the sleeve may be rotated to permit loading of the hollow cups with a suitable mixture, and after loading and freeze drying, the sleeve is rotated to seal the individual cups, and protect the contents of the cups during storage and shipment, until time of use.

Conveniently the ends of the cylinder have a diametral lug on at least one end and preferably both ends, which lugs are adapted to fit into a rack so that a plurality of cylinders may be simultaneously manipulated by a user. It is convenient to have a group of cylinders in a rack assembly for incubation and evaluation, and often for loading.

In use it is preferred that each cylinder containing different concentrations of a single antibiotic so that the susceptability of a microorganism to such antibiotic can be determined by inspection, by seeing in which of the cups the microorganism will grow even in the presence of a small concentration of the antibiotic.

By having a number of cylinders with cups in each, a separate antibiotic can be used in each cylinder. Different patients in a hospital may have different spectra of antibiotics to be tested. In production if a lot does not meet quality control standards, it is highly advantageous that only a single antibiotic in a single group of cylinders be suspect, so that rather than having to throw out a tray with a number of different antibiotics, only the one which is suspect is discarded. The versatility of multiple cylinders in a single test rack gives useful flexibility to the testing.

DRAWINGS

Other advantages and objects will be obvious from a more detailed description of the device as shown in the accompanying drawings in which.

Figure 1:
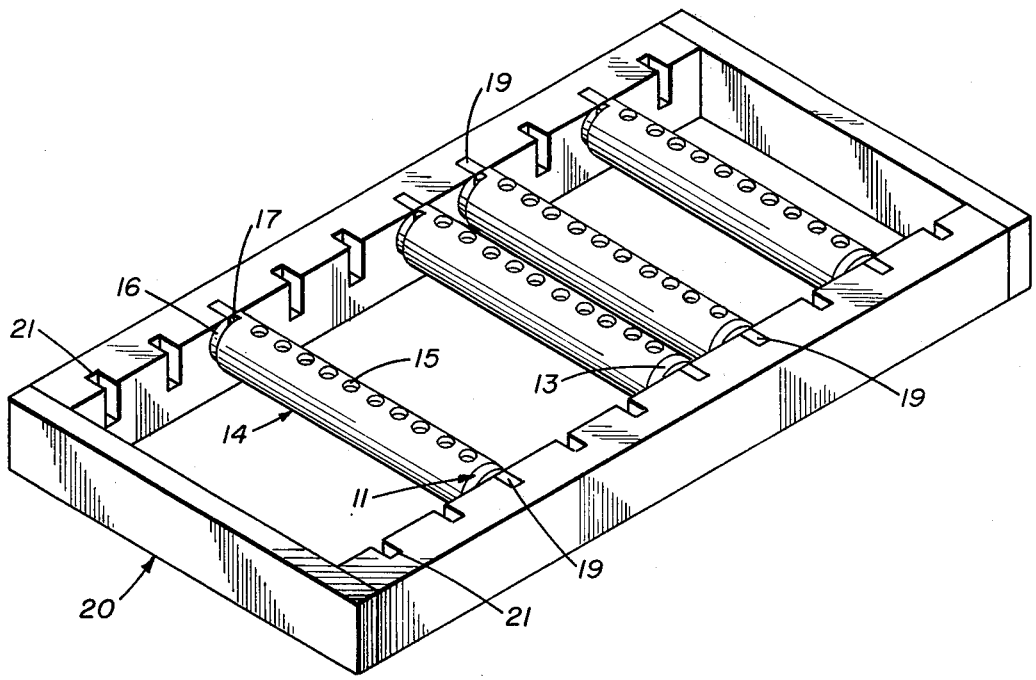
FIG. 1 is a pictorial view of a rack having therein several cylinders.
Figure 2:
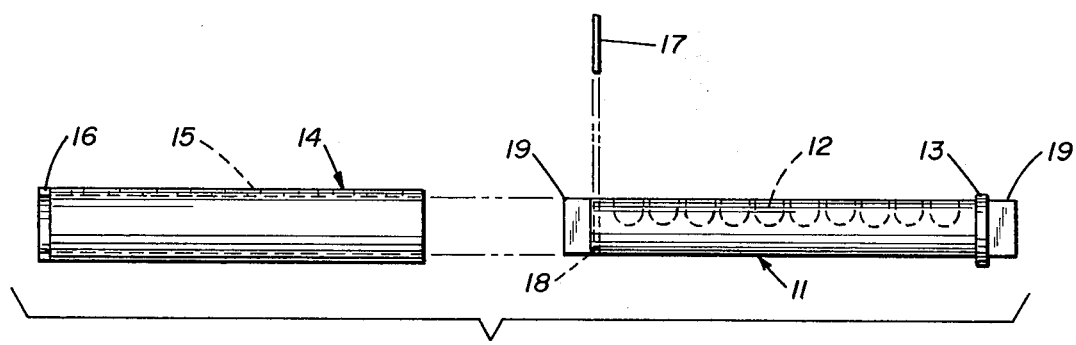
FIG. 2 is an exploded view of a single transparent solid cylinder showing a transparent plastic sleeve with its indexing pin withdrawn from the cylinder.
Figure 3:
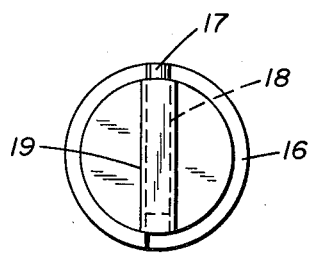
FIG. 3 is an end view of the assembled cylinder of FIG. 2 showing the orienting diametral lug on the end of the cylinder.

As shown in FIGS. 1 and 2 a transparent solid cylinder 11 of a biologically inert plastic has formed along one cylindrical element thereof a series of hollow cups 12. Preferably these cups are uniformly spaced and conveniently there are ten or eight such cups in a series along one element of the cylinder. Adjacent to one end of the cylinder is a positioning shoulder 13 which is conveniently but not necessarily formed integral with the transparent plastic cylinder 11 and is of slightly larger diameter so that it serves as a retaining and positioning shoulder for a transparent plastic sleeve 14. This transparent plastic sleeve 14 has an internal diameter just slightly larger than the outside diameter of the transparent solid cylinder so that it may rotate freely thereon. In this transparent plastic sleeve 14 along a single element thereof is a series of loading apertures 15 which are spaced to cooperate with the hollow cups 12 in the transparent solid cylinder 11. One end of the transparent plastic sleeve rests against positioning shoulder 13 and is axially positioned thereby. In the other end of the transparent plastic sleeve is a cut out section 16, conveniently just a slight shortening of about half of the transparent plastic sleeve which cooperates with an indexing pin 17 in an indexing pin hole 18. The indexing pin is slightly longer than the diameter of the transparent plastic cylinder and positioned so that when the indexing pin 17 is placed in the indexing pin hole 18, the end of the pin sticks up about the thickness of the transparent plastic sleeve. Thus, the cut out section of the transparent plastic sleeve permits the sleeve to rotate on the cylinder, and the angular relationships are such that when rotated in one direction, the cut out section positions the sleeve with the loading apertures in coordinate relationship with the hollow cups and when rotated in the other direction, the sleeve rotates approximately 180° to close the hollow cups for transportation, storage and incubation. If the cut out section is not greater than 180°, the pin may be placed with the entering end touching or almost touching the sleeve so that the pin cannot be driven in too far and yet permits approximately 180° rotation of the sleeve, and prevents the sleeve from slipping off the cylinder.

On each end of the plastic cylinder 11 is an orienting means, preferably a diametral lug 19. This lug is conveniently what might be considered a slightly thickened diameter of the cylinder forming a tongue which protrudes from the end of the cylinder. By having such a lug 19 on each end and parallel to the axis of the cups, a group of cylinders may be oriented in parallel relationship in a rectangular rack 20.

Conveniently the rectangular rack 20 consists of the four sides of an open box, without top or bottom, with a series of slots 21 formed in opposite sides of the rack of such size as to hold the diametral lugs 19 on a cylinder 11.

As shown in FIG. 1 there is a series of ten such slots 21 to hold the lugs 19 on the ends of ten cylinders 11 in a single rack for storage, manipulation, inoculation, culturing and inspection.

As shown in FIG. 1, only four cylinders are present; as in use the number of cylinders corresponds to the number of tests being run at one time. Frequently a single patient will have from three to ten different antibiotics cultured at one time. Preferably but not essentially the depth of the rack is such as to hold a cylinder, but not the sleeve, so that the sleeve extends slightly above the level of the top of the racks so that a group of the racks may be stacked vertically and the slight elevation of the sleeves will prevent the upper racks from sliding, thus aiding in ease of stacking and manipulation. The slots are cut deep enough to permit the diametral lugs to enter to the desired depth, with no binding, but avoiding undue lost motion. The rack may be made from a single molding, or built up from plastic bars. Conventional construction techniques are used.

Although racked so that a group of cylinders may be cultured and observed at one time, each cylinder is independently loaded and cultured, so that in effect a large number of independent tests are being simultaneously conducted.

Figure 4:
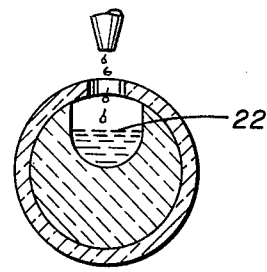
FIG. 4 is a cross-section of a cylinder showing a cup being filled with an antibiotic solution.
Figure 5:
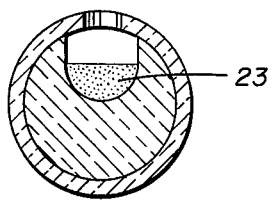
FIG. 5 is a cross-section view showing a cup in which the antibiotic has been dried down to a sponge.
Figure 6:
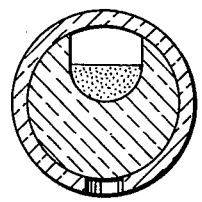
FIG. 6 is a cross-sectional view showing the dried sponge with the sleeve turned to close the cup for transportation and storage.

As shown in FIG. 4 each individual cup is loaded with an antibiotic solution 22. The concentrations of the antibiotic in each cup in a cylinder will normally be different. These are subjected to a standard freeze and dry cycle to lyophilize or freeze-dry the antibiotic solution. A typical cylinder containing the frozen-dried antiobiotic in a suitable gel is shown in FIG. 5. The dried gel with the antiobiotic is a cotton-candy like sponge 23. The transparent plastic sleeve is rotated to close the cap for transportation and storage, as shown in FIG. 6.

Figure 7:
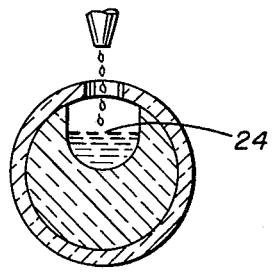
FIG. 7 shows the dried sponge in a cup having added thereto a culture medium and an inoculum.

At the time of use the sleeve is rotated back until the loading aperture 15 is opposite to the hollow cup 12 at which time a culture medium and/or test organism 24 is added as shown in FIG. 7.

The sleeve is rotated to close the cups after which a group of cylinders are conveniently placed in a rack for incubation. After a suitable incubation period the cylinders are inspected either by the human eye or automatic optical means to determine the growth of microorganisms in the individual cups.

Figure 8:
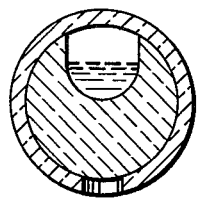
FIG. 8 shows a clear liquid containing an inoculum in a culture medium, and in which no growth has occured.
Figure 9:
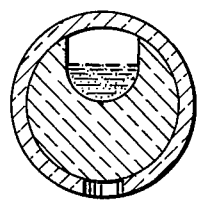
FIG. 9 is a cross-sectional view showing the same cup in which a microorganism has grown so as to cloud the solution.

FIG. 8 shows a clear liquid such obtained at the time of loading and before incubation or in those cups in which the level of the antibiotic is high enough to prevent growth of the microorganism, or a blank which has no inoculum or antibiotic, and is used to test sterility. If the microorganism grows the solution becomes cloudy as shown in FIG. 9. A skilled observer can observe a rack containing ten cylinders having ten cups each therein and as rapidly as the results can be written down, observe the cups in which growth has been inhibited, and thus the susceptability of the test microorganism to each antibiotic.

Figure 10:
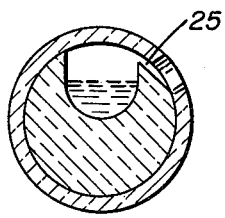
FIG. 10 is a cross-section of an alternative cylinder construction in which an air vent is formed to insure that the microorganism is subject to aerobic conditions.

FIG. 10 shows an alternate construction in which an air vent 25 is formed in the edge of the cup in a cylinder so that the sleeve may be partly rotated to prevent a chance contamination from air born microorganisms and yet permit the access of air, where it is essential that the microorganism be subjected to aerobic conditions.

In use, it is convenient to have ten cups each of which will hold 0.1 ml of solution when about half full. Because the quantities of antibiotics are so small, to insure that the antibiotic does not dry down to invisibility, it is preferable that the antibiotic be mixed with a gel in the diluent which will hold the antibiotics in the cup during storage until time of use. Conveniently a gel as poly(vinyl pyrrolidone) is used. A constant quantity of poly(vinyl pyrrolidone) is used for each of the ten cups in a series. The two cups are preferably left without antibiotic. One cup is not inoculated and is used as a sterility check, another one has no antibiotic and is used as a zero antibiotic level for uninhibited growth of the microorganism. The other eight are filled with antibiotics using a well known serial dilution technique—namely each succeeding cup conveniently is charged with twice as much antibiotic as the preceeding cup, so that a wide range of concentrations is obtained.

After filling in a cylinder, the cylinder is placed in a cold chamber to freeze the solution, which is then evacuate and dried by sublimation. This leaves the antibiotic in a dried gel. After drying, the sleeve is rotated on the cylinder to close the individual cups, and the cylinder stored until time of use.

Conveniently, the filling is done using aseptic techniques so that by first sterilizing the cylinder and sleeve assembly using ethylene oxide and filling sterilely, an assembly is obtained in which there are no chance contaminants. A group of cylinders may be placed in an envelope and kept sterile until time of use, or other methods may be used for maintaining sterility between manufacture and use.

At the time of use the cups have added thereto the culture medium and the test organism.

Because different laboratories desire to use different culture media and different culture media may be required for different organisms, it is convenient to add the culture medium at the time of use. Where the scale of operations is sufficient to warrant, the culture medium may be added with the antibiotic, and frozen and dried, so that only water need be added at the time of use.

The test microorganism may be mixed with the culture medium or may be added separately to each cup. The inoculum may be added before, with or after the culture medium.

The antibiotics or chemotherapeutic agents to be tested are listed in some of the prior art patents and include any of the antibiotics and chemotherapeutic agents which control the growth of microorganisms and are in use in either a hospital or a research facility. Similarly the microorganisms tested for sensitivity towards particular antibiotics or therapeutic agents are those which in either research programs or clinical practice are found to present questions warranting investigation as to antibiotic susceptability.

To retain the small quantities of antibiotics used in the various test cups a gel as a binder which when dried forms a sponge is conveniently used as a carrier. One such gel binder is poly(vinyl pyrrolidone). On freeze-drying a sponge that resembles cotton candy is formed. It is sufficiently bulky to be easily seen, and hence its presence is readily visually checked. The antibiotic itself could not be readily observed with the unaided eye. The sponge if shaken may become loose, but by orienting the cups vertically when the sleeve is rotated to permit filling, the sponge in each cup remains in the cup and dissolves in the added liquid.

EXAMPLE

Into the first of ten 4 liter flasks was added 6 g. of poly(vinyl pyrrolidone) (Povidone USP) and 3 liters of triple distilled water. In each of the other nine flasks was added 3 g. of poly(vinyl pyrrolidone) and 1,500 ml. of water.

To the first flask was added 206.25 mg. of tetracycline hydrochloride. The flask was shaken until the contents were dissolved and uniformly distributed. One half of the contents of the first flask were then added to the second flask and the contents shaken until uniform. One half of the contents of the second flask were then added to the third flask and the contents of the third flask shaken until uniform. This procedure was followed thus diluting by one half the concentration in each succeeding flask until the ninth flask was reached. This gave a serial two-fold dilution.

The contents of each flask were sterilely filtered into two liter reagent bottles which were capped and kept in an ice-water bath for filling using sterile techniques. Filling should not be delayed. The solutions should remain stable and without change for at least 24 hours if kept cold but it is preferably that they be filled immediately.

2/10 ml. of the contents of each of flasks 1 to 10 were filled into the respective hollow cups of one cylinder. The cylinder was placed in a rack. The cups in a total of 5,000 cylinders were filled, and placed in racks, and the racks placed in a cold chamber. The chamber was pre-chilled and the freezing chamber maintained at colder than $-40°$ C with the shelf cooling being maintained at maximum until all trays were frozen solid. This should occur in less than 12 hours. After freezing, the chamber was evacuated to 100 microns, or less, after which the shelf temperature is raised to $+10°$ C and continued at this temperature until temperature probes in the cylinder assembly indicate that the temperature was within $5°-10°$ C of the temperature of the shelves. The shelves were then warmed to $30°$ C. After the cylinders had warmed up, the shelf temperature was increased to $40°$ C and held for four hours. At this point the contents of each cylinder are thoroughly dried. Using sterile techniques the transparent plastic sleeves were rotated to close the cylinders and the cylinders are placed in polyethylene bags with a dried silica gel packet to maintain dryness. One 5 g. silicate gel packet was used for each set of five cylinders. Groups of cylinders of a convenient number, here ten, were packed in a foil pouch and the foil pouch sealed to maintain dryness.

The cylinders were labelled with the name of the antibiotic, here tetracycline hydrochloride. The sealed assembly may be kept at room temperature until time of use. At the time of use the packages are opened, cups in each cylinder filled with 2/10 ml. of a selected culture medium, and inoculated with a small drop of the test organism, then incubated for an appropriate cycle.

On inspection the growth of the organism can be seen and the concentrations of the antibiotic required to inhibit the growth ascertained by inspecting the cups in which growth has been inhibited.

When filled in this fashion, the cups contain:

TABLE

| Cup No. | |
|---|---|
| 1 | 12.5 γ antibiotic + 10% excess plus 400γ Povidone |
| 2 | 6.25 γ antibiotic + 10% excess plus 400γ Povidone |
| 3 | 3.125γ antibiotic + 10% excess plus 400γ Povidone |
| 4 | 1.56 γ antibiotic + 10% excess plus 400γ Povidone |
| 5 | 0.78 γ antibiotic + 10% excess plus 400γ Povidone |
| 6 | 0.39 γ antibiotic + 10% excess plus 400γPovidone |
| 7 | 0.195γ antibiotic + 10% excess plus 400γ Povidone |
| 8 | 0.098γ antibiotic + 10% excess plus 400γ Povidone |
| 9 | 0.049γ antibiotic + 10% excess plus 400γ Povidone |
| 10 | 0.00 γ — — |

Similarly other cylinders were filled with dilutions of other antibiotics starting with 206.250 units of sodium penicillin G; 206.25 mg. sodium methicillin; 206.25 mg of sodium ampicillin; 206.25 mg. erythromycin base, and 206.25 mg. clindamycin.

The above is typical of antibiotics to be tested. Other antibiotics, either those known or those yet to be discovered may be used—and if the anti-antibiotics require a range other than that listed, the concentration may be modified—but with the wide range covered by the nine dilutions in the cavities, the proper dosage of most antibiotics will be obtained.

The tenth cup has no antibiotic and hence if inoculated with the test microorganism, shows the growth of the microorganism under uninhibited conditions; or if not inoculated is used to show that no contaminants are present.

The number of cylinders and choice of cylinders, each with a different antiobiotic, depends upon the preferences of the medical staff of the using facility.

Having thus described the present invention, the invention is set forth in the following claims in which all parts are by weight unless otherwise specified:

I claim:

1. An antibiotic susceptability testing cylinder assembly comprising a transparent solid cylinder of biologically inert plastic having therein, along one cylindrical element, a series of hollow cups radially formed into the plastic of the cylinder, and orienting means at at least one end of the cylinder, and fitting over said cylinder a transparent plastic sleeve, having a series of loading apertures along one cylindrical element, spaced in cup loading configuration for one rotational position of the sleeve, and indexing means to arrest rotation of the sleeve with the loading apertures in loading relationship with the cups in one direction of rotation, and in sealing relationship in the other direction rotation.

2. The cylindrical assembly of claim 1 in which the orienting means is a diametral lug on each end of said cylinder.

3. The cylinder assembly of claim 2 additionally comprising a rectangular plastic rack having a series of pairs of slots on opposed parallel sides, each pair of slots being of such size and shape as to hold the diametral lugs of one cylinder, so that a series of parallel cylinders fit into and are held by the rack.

4. The cylinder assembly of claim 3 in which the indexing means consists of a pin fitting into a hole near one end of said cylinder, which cooperates with a cut out section of the plastic sleeve, so as to permit about a half turn of the sleeve, and said cylinder has a sleeve positioning shoulder to retain the sleeve at the other end of the cylinder.

5. The cylinder assembly of claim 4 in which at least some of the cups contain a plurality of dilution levels of a dried antibiotic retained in the cup by a dried water soluble gel.

6. The cylinder assembly of claim 1 in which the cylinder has a slight molding draft, of about 1 to 3°, and the sleeve the same molding draft, so that the cylinder and sleeve may be molded, and the mandrel withdrawn from the sleeve, and the cylinder from its mold.

* * * * *